United States Patent [19]

Carlson

[11] Patent Number: 4,793,179
[45] Date of Patent: Dec. 27, 1988

[54] APPARATUS AND METHOD FOR PRESSURE BURST TESTING OF A VESSEL

[75] Inventor: Ernest M. Carlson, Minnetonka, Minn.

[73] Assignee: Honeywell Inc., Minneapolis, Minn.

[21] Appl. No.: 154,418

[22] Filed: Feb. 10, 1988

[51] Int. Cl.$^4$ .............................................. G01L 5/14
[52] U.S. Cl. .......................................... 73/167; 73/35; 73/753
[58] Field of Search .................. 73/167, 168, 137, 11, 73/12, 58, 753, 754, 865.9, 154, DIG. 4, 35

[56] References Cited

U.S. PATENT DOCUMENTS

| | | | |
|---|---|---|---|
| 2,362,484 | 11/1944 | Hickman | 73/167 |
| 3,043,137 | 7/1962 | Clark et al. | 73/167 |
| 3,693,432 | 9/1972 | Stewart et al. | 73/167 |
| 3,863,499 | 2/1975 | Von Boutteville | 73/167 |
| 3,919,880 | 11/1975 | Seyd et al. | 73/49.8 |
| 3,946,607 | 3/1976 | Panella | 73/35 |
| 3,960,018 | 6/1976 | Change et al. | 73/167 |
| 4,088,907 | 5/1978 | Jones et al. | 310/333 |
| 4,143,617 | 3/1979 | Youngren | 73/35 |
| 4,263,807 | 4/1981 | Brown et al. | 73/167 |
| 4,317,373 | 3/1982 | Goes et al. | 73/167 |
| 4,356,720 | 11/1982 | Betts | 73/37 |
| 4,419,881 | 12/1983 | Gentiluomo | 73/37 |

*Primary Examiner*—Harvey C. Hornsby
*Assistant Examiner*—Corinne M. Reinckens
*Attorney, Agent, or Firm*—Roger W. Jensen

[57] ABSTRACT

An apparatus for pressure burst testing of a hollow vessel, such as a gun barrel, includes a hydraulic cylinder assembly and a test mandrel mounted on a frame in axial alignment. The test mandrel includes a hollow sleeve stationarily mounted on the frame and having an outer end adapted to receive thereover the vessel such that the portion of the vessel to be tested extends beyond the outer end. An elongated drawbar is disposed coaxially within the sleeve and is attached to a reciprocally driven piston of the cylinder assembly. At an outer end, the drawbar extends beyond the sleeve outer end and is coextensible within the vessel portion to be tested. The piston and drawbar therewith are movable relative to the sleeve through respective pressure-generating and pressure-releasing strokes for causing radial expansion and contraction of a resiliently deformable annular member, preferably formed of one or more ring-shaped elements of elastomer material, and thereby respective application and release of pressure by the deformable material against the interior of the vessel portion to be tested. The deformable member is mounted on the drawbar and disposable within the vessel portion to be tested. Also, the deformable member is located between the sleeve outer end and the drawbar outer end such that movement of the drawbar relative to the sleeve causes the respective pressure-generating and pressure-releasing radial expansion and contraction of the deformable member.

31 Claims, 4 Drawing Sheets

APPARATUS AND METHOD FOR PRESSURE BURST TESTING OF A VESSEL

BACKGROUND OF THE INVENTION

1. Field of the Invention

The present invention generally relates to burst testing of pressure vessels and, more particularly, is concerned with a apparatus and method for pressure burst testing of a hollow vessel by mechanically applying pressure thereon.

2. Description of the Prior Art

In the course of manufacturing any pressure vessel which ultimately will be placed in the hands of or physical presence of human beings, certain minimum safety standards must be adhered to. The standards now established by ASME-Boiler and Pressure Code "An American National Standard"—Section V entitled "Nondestructive Examination"—dated July 1, 1983 require that varying safety standards (expressed as safety factors) must be met by any manufacturer prior to any product being issued for actual use. These safety standards may cover operation or use of the supplied product in diverse environments (temperature, humidity, rapidity and range of changes in both) and under varying pressures applied at varying rates of pressure increases and decreases. Impact and vibration effects may also be factors in meeting minimum performance standards.

This diverse array of conditions for replicating actual use situations has more or less been reproduced successfully and satisfactorily for most pressure vessel product testing by the manufacturers involved, using the same pressure applying medium as would be used in the actual application of the product. However, in the case of a pressure vessel or chamber, which is pressurized by an explosive charge, particularly a "designed for one time use only" vessel, i.e., gun barrel, satisfactory results are yet to be reached due to several drawbacks.

One drawback is that actual testing at required-use pressures stresses the product sufficiently to make it unusable for the once-only application it was designed for. Another drawback is that "pressure over specified rate and time" static type tests are difficult, if not impossible, to manage consistently when using explosives. Hydrostatically replicated pressure building involves expansion/leak problems, problems of contamination with a medium of porous or laminated composite materials used in the product being tested, and problems of shrapnel-like reactions when the product fails catastrophically under test load. Still another drawback is that explosive-generated pressures are exceedingly dangerous in the areas of actual test (again, shrapnel generation upon failure), test procedure setup (explosives loading and arming), handling, shipping, and transferring of explosive materials. A further drawback is that explosive pressure generation for test purposes, particularly under requirements of a multi-environment/multi-test program, is economically prohibitive in that testing costs could easily exceed the product's base value many times over. Also, excessive insurance and special facility costs would also be factors of consideration.

This particular field of pressure generation (such as by explosives) has in the last decade fallen far short of the needs of manufacturers who are now working with exotic materials and materials processes which are oftentimes very costly and likewise time consuming to produce. This is particularly the case in armament development and related technology. A demand has resulted for a nondestructive, repeatable, reliable, consistent, controllable, and economical method of replicating explosively generated pressures within varying designs of vessels or vessel-like chambers. Prior art techniques of pressure testing vessels, i.e. gun and cannon barrels and breaches, such as represented by the methods and apparatuses disclosed in U.S. Pat. Nos. to Von Boutteville et al (3,863,499), Seyd et al (3,919,880), Brown et al (4,263,807), Betts (4,356,720) and Gentiluomo (4,419,881), have failed to meet this urgent need.

SUMMARY OF THE INVENTION

The present invention provides a pressure burst testing apparatus and method designed to satisfy the aforementioned needs. In the apparatus and method of the present invention, the use of explosives, oil, gases or water for pressure generation is replaced by a reusable, expandable, solid but flexible semi-static plastic material which, when pressure is applied to it mechanically, behaves and satisfactorily replicates the pressure application characteristics of the aforementioned prior modes (explosives or hydraulics in some form).

In such manner, the present invention eliminates the possibility of oil leaks from static pressure testing. Also, in testing composite laminated barrels, test failures due to oil seepage through delamination in the barrel wall prior to the barrel catastrophically bursting at acceptable pressure levels are avoided. Further, the need to use hazardous propellant type explosives and components which require test range areas for safety and noise is obviated. Most advantageously, the present invention permits dynamic testing in the facility producing the barrel or pressure vessel.

Accordingly, the present invention is directed to an apparatus for pressure burst testing of a hollow vessel. The pressure burst testing apparatus comprises a test mandrel and powered reciprocable means mounted on a frame in axial alignment with one another.

More particularly, the test mandrel includes a hollow sleeve, an elongated drawbar, and a resiliently yieldable deformable member. The hollow sleeve has an outer end adapted to receive thereover a hollow vessel such that a portion of the vessel to be tested extends beyond the sleeve outer end. The drawbar is disposed within the hollow sleeve and has an outer end extending beyond the outer end of the sleeve. The deformable member is mounted on the drawbar and is coextensible within the vessel portion to be tested when the vessel is received over the sleeve outer end and diameter. At least one of the drawbar and sleeve is disposed for movement relative to the other through respective pressure-generating and pressure-releasing strokes.

Further, the deformable member has opposite ends and is mounted between and in contact at its opposite ends with the sleeve outer end and the drawbar outer end. The deformable member is preferably in the form of one or more ring-shaped elements composed of elastomer material. The deformable member is adapted to expand radially so as to apply expansive mechanical pressure against the interior of the vessel portion to be tested upon relative movement of the sleeve add drawbar through the pressure-generating stroke which causes relative movement of the sleeve outer end and drawbar outer end toward one another and thereby application of compressive force against the opposite ends of the deformable member. Conversely, the deformable member is adapted to contract radially so as to release application of the mechanical pressure against the interior of tee vessel portion to be tested upon relative movement of the sleeve and drawbar through the pressure-releasing stroke which causes relative movement of the sleeve outer end and drawbar outer end away from one another and thereby release of application of compressive force against the opposite ends of the deformable member.

The powered reciprocable means of the pressure burst testing apparatus is operable to move the drawbar through the respective pressure-generating and pressure-releasing strokes for causing expansion and contraction of the deformable member. The powered reciprocable means includes a hydraulic cylinder assembly and power means connected in communication with a cylinder housing of the assembly and being actuatable to drive a piston of the assembly and the drawbar attached thereto through the respective strokes.

Also, the present invention is directed to a method for pressure burst testing of the hollow vessel. The testing method comprises the steps of: (a) providing a drawbar and a hollow open-ended sleeve in reciprocally movable relation to one another and with the drawbar extending through the sleeve such that an outer end of the drawbar extends beyond an outer end of the sleeve; (b) providing a resiliently yieldably deformable annular member about the drawbar between and in contact with an outer end of the sleeve and an outer end of the drawbar; (c) disposing a hollow vessel over the outer end of the sleeve such that a portion of the vessel to be tested extends beyond the sleeve outer end and over the deformable member mounted on the drawbar outer end; (d) moving the drawbar and sleeve relative to one another through a pressure-applying stroke so as to move the drawbar outer end and the sleeve outer end toward one another and apply a compressive force against opposite ends of the deformable member, causing the member to expand radially and apply an expansive mechanical pressure against the interior wall of the vessel portion to be tested; and (e) moving the drawbar and sleeve relative to one another through a pressure-releasing stroke so as to move the drawbar outer end and the sleeve outer end away from one another and release application of the compressive force against opposite ends of the deformable member, allowing the member to contract radially and release application of the mechanical pressure against the interior of the vessel portion. The testing method comprises the further step of: (f) sensing the mechanical pressure applied by the deformable member against the interior of the vessel portion to be tested.

These and other advantages and attainments of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the course of the following detailed description, reference will be made to the attached drawings in which.

DETAILED DESCRIPTION OF THE INVENTION

Figure 1:
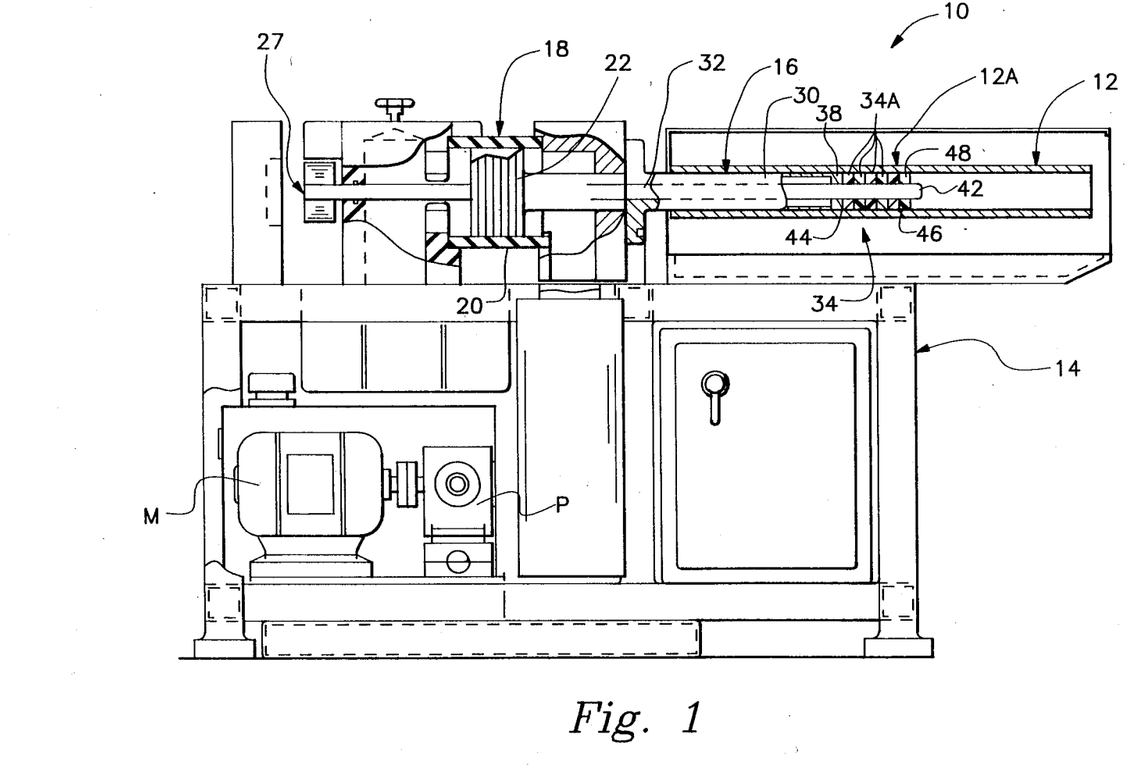
FIG. 1 is a side elevational view of a pressure burst testing apparatus constructed in accordance with the principles of the present invention.
Figure 2:
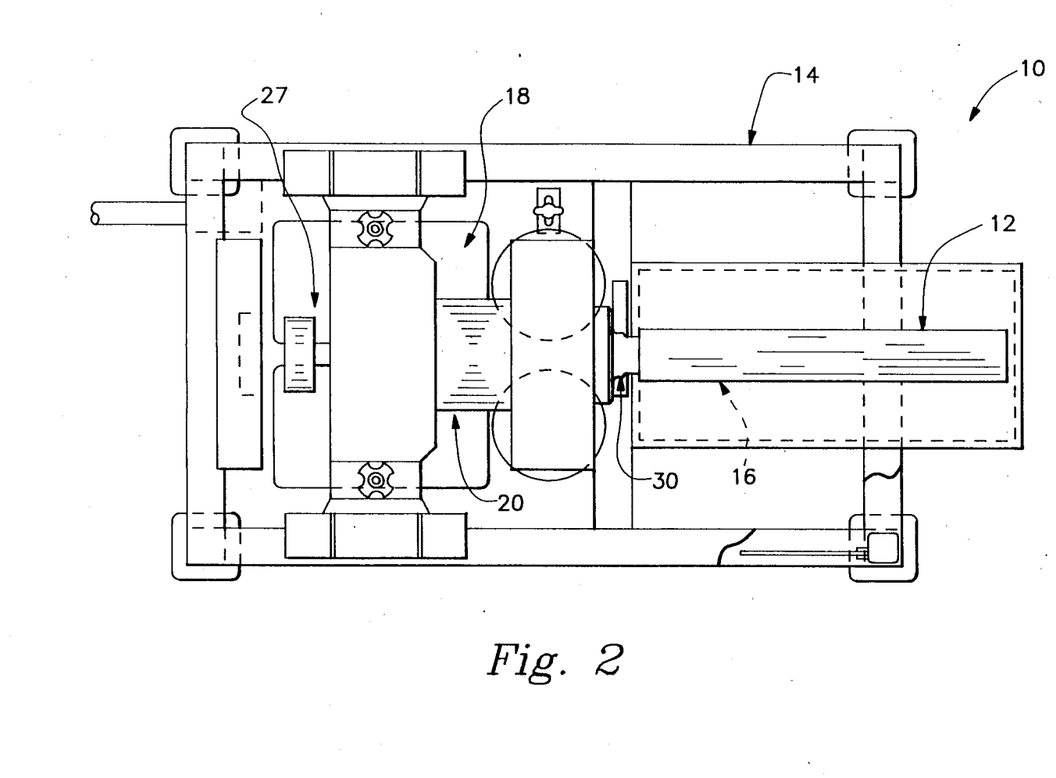
FIG. 2 is a top plan view of the apparatus of FIG. 1.
Figure 4:
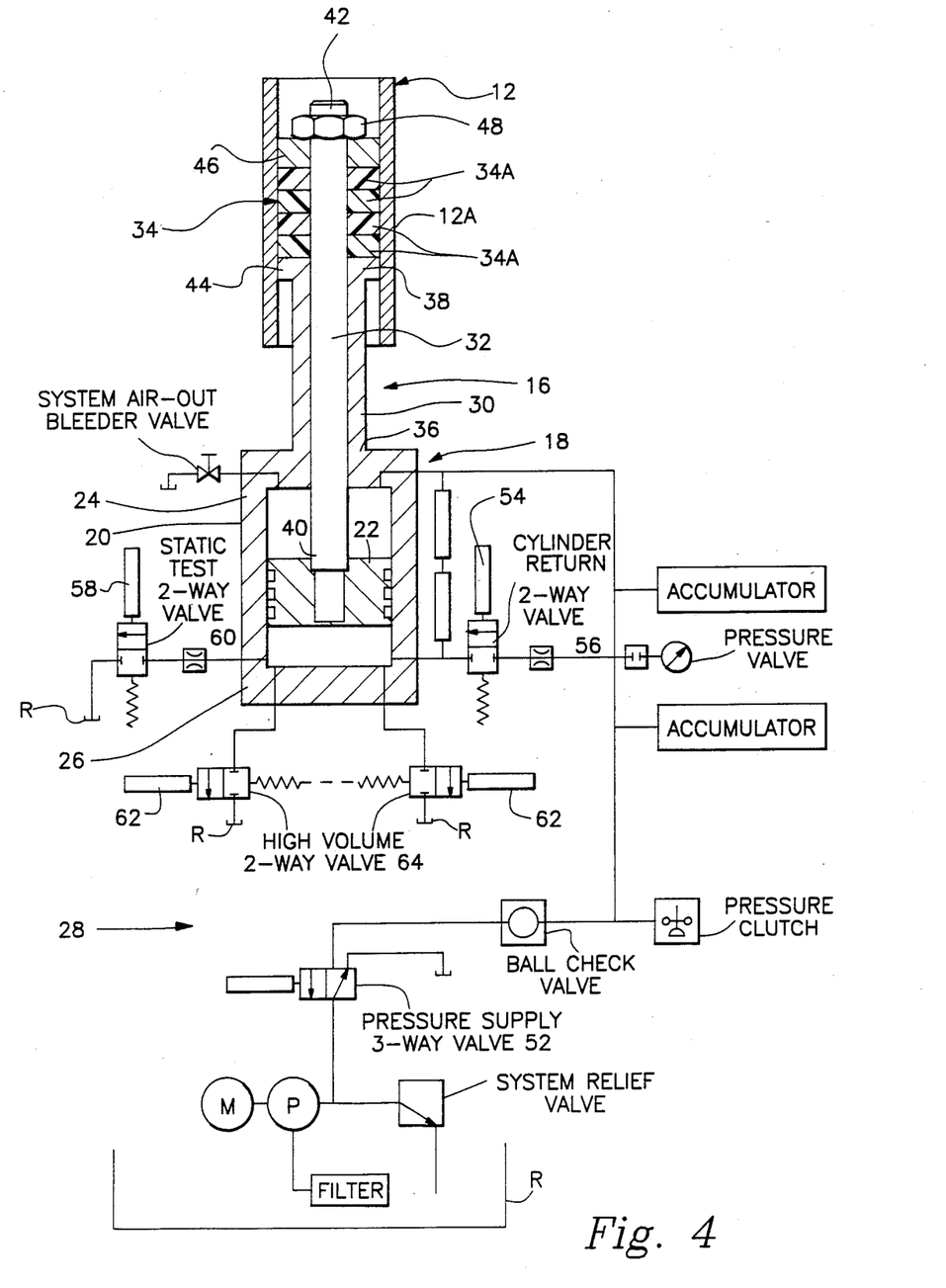
FIG. 4 is a schematic diagram of the test mandrel and the hydraulic circuit of the apparatus associated therewith

Referring now t the drawings, and particularly to FIGS. 1 and 2, there is shown a pressure burst testing apparatus, being generally designated by the numeral 10 and constituting the preferred embodiment of the present invention. The apparatus 10 may be used for pressure burst testing of a wide variety of hollow pressure vessels. The hollow vessel illustrated in FIGS. 1, 2 and 4 is a gun barrel 12. Examples of other possible vessels that can be tested by the apparatus 10 are rocket launcher and motor tubes, recoilless weapon tubes, mortar and cannon barrels, heat exchanger tubes, nuclear reactor tubes and other types of pressure vessels.

In its basic components, the testing apparatus 10 includes a frame 14 upon which are mounted a test mandrel 16 and a hydraulic cylinder assembly 18 disposed in axial alignment with the test mandrel. The hydraulic cylinder assembly 18 is composed of a hollow cylinder housing 20 mounted on the frame 14 and a cylindrical piston 22 mounted in the cylinder housing 20 in spaced relation to and between opposite forward and rearward ends 24, 26 thereof. In a forward and aft direction along a common axis A of the mandrel 16 and assembly 18, the piston 22 is capable of undergoing reciprocal movement through pressure-generating and pressure-releasing strokes within the cylinder housing 20. A stop mechanism 27 at the rear of the hydraulic cylinder assembly 18 is adjustable for control of the piston stroke and element 34 expansion.

Also, the testing apparatus 10 includes power means, generally indicated by the numeral 28 in FIG. 4, connected in communication with the opposite forward and rearward ends 24, 26 of the cylinder housing 20 and being actuatable to feed hydraulic fluid under pressure to the housing ends to drive the piston 22 through its respective strokes. The power means 28 will be described in detail later on.

As mentioned above, the test mandrel 16 of the testing apparatus 10 is coaxially aligned along common axis A with the hydraulic cylinder assembly 18. More particularly, the test mandrel 16 includes an elongated hollow open-ended sleeve 30, an elongated rigid member or drawbar 32, and a deformable member 34.

Figure 3:
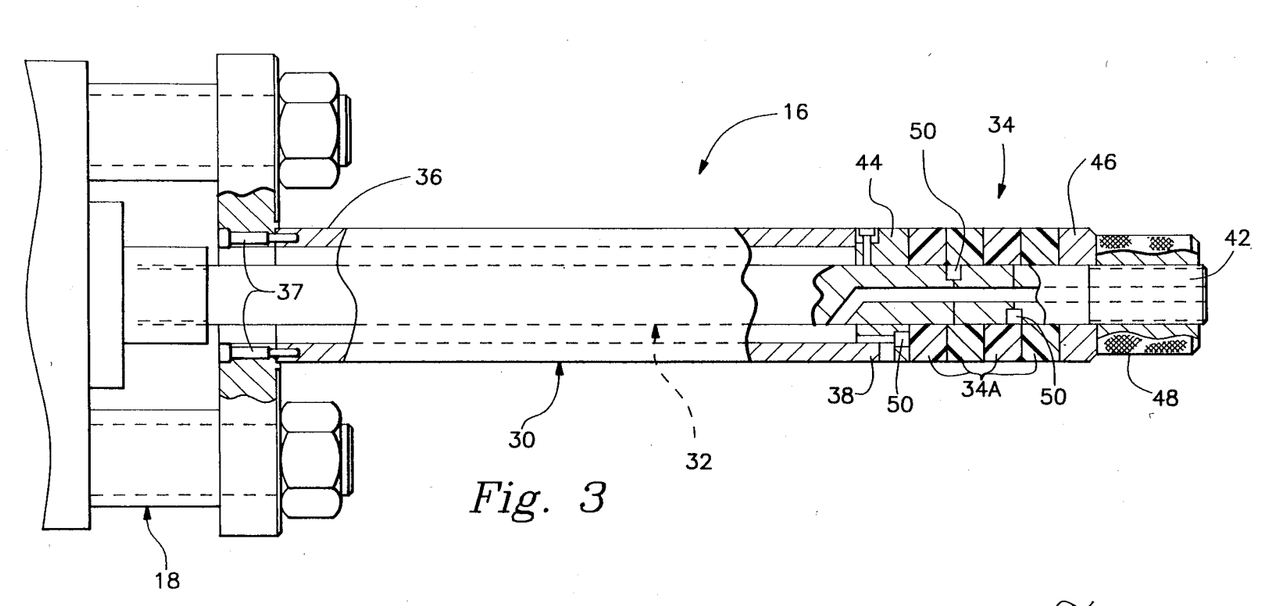
FIG. 3 is an enlarged fragmentary view, partly in section, of a test mandrel employed in the apparatus of FIG. 1.

Preferably, as seen in FIG. 3, the hollow sleeve 30 of the test mandrel 16 is stationarily mounted on the frame 10 in cantilevered fashion with a rearward or inner end 36 of the sleeve being rigidly connected to the cylinder housing 20 by fasteners 37. At a forward or outer end 38, the sleeve 30 is adapted to receive thereover the hollow vessel 12 in such manner that a portion 12A (see also FIG. 4) of the vessel 12 to be tested extends beyond the sleeve outer end 38.

The drawbar 32 of the test mandrel 16 is disposed coaxially within and extends through the open-ended sleeve 30 The drawbar 32 functions as an extension of a piston rod being rigidly attached at its rearward or inner end 40 to the forward side of the piston 22. At its forward or outer end 42, the drawbar 32 extends beyond the outer end 38 of the hollow sleeve 30 and is coextensive with the vessel portion 12A to be tested. Due to its attachment to the piston 22, the drawbar 32 is movable therewith relative to the stationary sleeve 30 through the respective pressure-generating and pressure-releasing strokes.

As shown in FIG. 1 but in greater detail in FIGS. 3 and 4, the sleeve 30 and drawbar 32 at their respective outer ends 38 and 42 have attached thereon annular header or end plates 44 and 46. In the normal rest position of the drawbar 32 relative to the sleeve 30, the drawbar end plate 46 is spaced axially from the sleeve end plate 44.

The resiliently yieldably annular deformable member 34 of the test mandrel 16 is mounted about the drawbar 32 and located between the sleeve and drawbar end plates 44, 46. At such location, the deformable member 34 is carried on the portion of the drawbar 32 which extends beyond the outer end 38 of the sleeve 30 and, thus, is disposed within the vessel portion 12A to be tested. A nut 48 is threaded on the drawbar outer end 42 to retain the drawbar end plate 46 thereon and the deformable member 34 at its axially displaced opposite ends disposed respectively in contact with the sleeve and drawbar end plates 44, 46. The outside diameter of the deformable member 34 is slightly less than the inside diameter of the vessel 12 to be tested.

Preferably, the deformable member 34 is formed of a plurality of doughnut-, puck- or ring-shaped elements 34A composed preferably of polyurethane elastomer material. When mechanical pressure is applied in compressive fashion to either one or both opposite ends of the deformable elastomer member 34 so as to draw or squeeze its elements 34A together, the member radially expands increasing its outside diameter. Once the compressive force is released, the material returns to its original outside diameter size. The deformable member 34 may be shaped externally to conform to and fill the shape of the cavity of the vessel being pressure tested so long as it is possible to insert the deformable member 34 into and afterwards withdraw it from the vessel.

The urethane used for the annular deformable member 34 could vary in chemical formula depending on the maximum pressure range sought. The specific urethane formula AMS 3571/6A-1984-Resin, polyether urethane (EU) casting flexible, solid, unfilled at 95 durometer "A" is specifically appropriate for pressure testing in the 20,000 to 30,000 psi applied pressure range, such being the range contemplated herein for pressure burst testing of the gun barrel 12 using the apparatus 10. When surface lubricated properly, this urethane product applies consistent, uniform, hydrostatic replicating pressure within the chamber or vessel being tested; and, when the mechanical confining force is released, the urethane elastomer returns to its original or former (smaller or natural) state and size. This allows immediate reuse of the test mandrel 16 on another vessel or for another test of different factors.

Thus, it is readily understood that the deformable member 34 is adapted to expand radially so as to apply the desired mechanical pressure against the interior of the vessel portion 12A being tested upon movement of the piston 22 and the drawbar 32 therewith through the pressure-generating stroke relative to the stationary sleeve 30. Such movement of the drawbar 32 causes axial movement of its outer end plate 46 toward the sleeve outer end plate 44 and thereby application of compressive force against the opposite ends of the deformable member 34 to produce such outward radial expansion thereof. Conversely, the deformable member 34 is adapted to contract radially so as to release application of the mechanical pressure against the interior of the vessel portion 12A upon movement of the piston 22 and the drawbar 32 therewith through the opposite, pressure-releasing stroke relative to the stationary sleeve 30. Such movement of the drawbar 32 causes axial movement of its outer end plate 46 away from the sleeve end plate 44 and thereby release of application of compressive force against the opposite ends of the deformable member to permit such inward radial contraction thereof.

The testing apparatus 10 further includes means in the form of electronic pressure transducers 50 embedded in the drawbar 32 and deformable member 34 which directly sense the mechanical pressure exerted by the elastomer deformable member 34 against the interior of the vessel portion 12A being tested. The electrical signals from the transducers 50 are transmitted to components (not shown) such as multichanneled data acquisition oscilloscope, multiplexers and computers. Various measurements can be made, such as pounds of pressure per square inch applied, specific rate and duration of pressure application, and shock pressure, pressure fall and rise response curves can be calculated.

FIGS. 3 and 4 illustrate some of the electrical and hydraulic components for actuating the piston 22 and the drawbar 32 therewith of the apparatus 10 through their pressure-generating and pressure-releasing strokes for carrying out the steps involved in the method of pressure burst testing of the vessel 12. The hydraulic circuit includes a motor M which operates a pump P to feed fluid under pressure from a reservoir R through a supply valve 52 to the forward end 24 of the cylinder housing 20 and the forward side of the piston 22 therein, or to both ends of the housing 20 and sides of the piston 22 if a cylinder return solenoid 54 has been actuated to open the cylinder return valve 56 connected thereto.

The power means 28 is operable in two modes: one is a static mode and the other is a dynamic mode. In the static mode, a static test solenoid 58 is actuated to open the static test valve 60 connected thereto. In the dynamic mode, dynamic test solenoids 62 are actuated simultaneously to open the high volume valves 64. In the static mode, a controlled gradual evacuation of fluid from the rearward end 26 of the cylinder housing 20 takes place, allowing a gradual increase in pressure to occur in the forward end 24 thereof. On the other hand, in the dynamic mode, an instantaneous (such as lasting only 5 milliseconds) evacuation of fluid from the rearward end of the cylinder housing occurs, allow an instantaneous increase in pressure in the forward end thereof.

Figure 5:
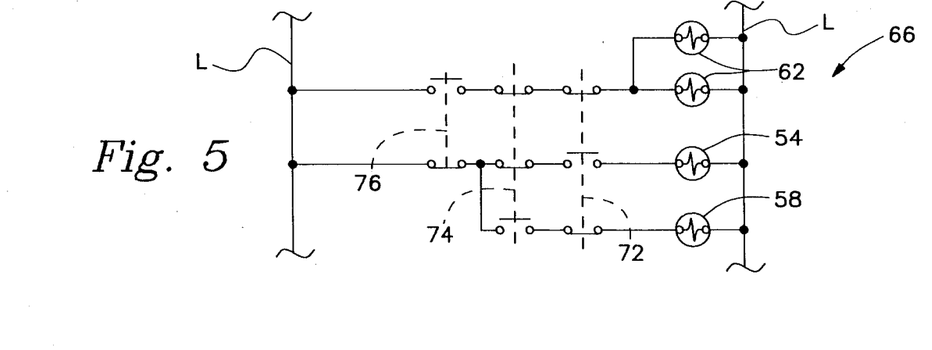
FIG. 5 is a schematic diagram of the portion of the electrical circuit of the apparatus which contains components for actuating components of the hydraulic circuit of FIG. 4.

The various solenoids and their valves are actuated by push buttons electrically connected to the solenoids and between electrical supply lines L of the electrical circuit 66, being illustrated in FIG. 5. A protective cover 68 (FIGS. 1 and 2) must be closed to actuates a solenoid 70 (FIG. 4) which opens the supply valve 52. The return of the piston 22 to its initial position is caused by depression of a push button 72 which actuates the cylinder return solenoid 54. The static test is started by depression of a push button 74 which actuates the static test solenoid 58. The dynamic test is started by depression of push button 76 which actuates the dynamic test solenoids 62. It can be seen that the circuit connections and switches associated with the push buttons are such that only on of the solenoids 54, 58 and 62 can be actuated at a given time.

To perform the steps of the method for pressure burst testing of the hollow vessel 12, the hollow sleeve 30, drawbar 32 and deformable member 34 are arranged as described above.. The hollow vessel 12 is placed over the outer end 38 of the stationary sleeve 30 such that the vessel portion 12A to be tested extends beyond the sleeve outer end 38 and over the deformable member 34 mounted on the drawbar otter end 42. The protective cover 68 is then closed and the solenoid 70 is actuated to open the supply valve 52.

Depending upon whether the static or dynamic mode of testing is to be carried out, either push button 74 or 76 is depressed, causing the piston 22 and drawbar 32 therewith to move relative to the sleeve 30 through the pressure-applying stroke (toward the left in FIG. 1 and toward the bottom in FIG. 4) so as to move the drawbar end plate 46 toward the sleeve end plate 44 and apply a compressive force against opposite ends of the deformable member 34. Application of the compressive force causes the member 34 to expand radially end apply an expansive mechanical pressure against the interior of the vessel portion 12A to be tested. Once pressurizing of the vessel 12 is completed, the push button 72 is depressed, causing the piston 22 and drawbar 32 therewith to then move in reverse fashion relative to the hollow sleeve 30 through a pressure-releasing stroke so as to move the drawbar end plate 46 away from the sleeve end plate 44 and release application of the compressive force against opposite ends of the deformable member 34. Release of the compressive force allows the deformable member 34 to contract radially to its original diameter size and release application of the mechanical pressure against the interior of the vessel portion 12A.

The method of the present invention, due to its controllability as regards pressure and time duration range, is believed to be the only method whereby particularly exotic "laminated construction" vessels may be produced, manufactured, tested and distributed under a qualification program involving acoustic or sonic inspection and evaluation wherein "actual use" pressure need not be actually applied. Instead, a nondestructive, lower, representative pressure can be used to establish the tested unit's "signature response" on predeveloped/worked-up time, pressure, and frequency curves giving behavioral characteristics at specifcially applied pressures.

Exotic laminate construction products do not lend themselves well to sustained hydraulic high-pressure testing as the elastic bonding agent will cold flow, releasing its bond to the fibers of the basic strength materials. This bond release causes a slow delamination and fluid or moisture penetration or leakage. This delamination is not always detectable sonically or if oil has penetrated the delamination the resultant contamination of the product is unacceptable.

Explosive dynamically applied pressure is, of course, not compatible to sonic testing due to excessive "noise" generation and instantaneous catastrophic nature of the application. Chambers or vessels designed as once-only used products (such as specific weaponry) which require the use of costly exotic methods and materials in their construction, almost always require that sonic test response curves be used in their evaluations, and the expanding urethane mandrel method of pressure application disclosed herein is the most or only compatible method that tests yet saves the product, does not contaminate it, is safe to test personnel, does not require extraordinary facilities, and is extremely economical and reusable.

It is thought that the present invention and many of its attendant advantages will be understood from the foregoing description and it will be apparent that various changes may be made in the form, construction and arrangement of the parts thereof without departing from the spirit and scope of the invention or sacrificing all of its material advantages, the form hereinbefore described being merely a preferred or exemplary embodiment thereof.

Having thus described the invention, what is claimed is:

1. In an apparatus for pressure burst testing of a hollow vessel, a test mandrel comprising:
   (a) a hollow sleeve having an outer end adapted to receive thereover a hollow vessel such that a portion of the vessel to be tested extends beyond said sleeve outer end;
   (b) an elongated drawbar disposed within said hollow sleeve and having an outer end extending beyond said outer end of said sleeve and being coextensible with the vessel portion to be tested when the vessel is received over said sleeve outer end, at least one of said drawbar and sleeve being disposed for movement relative to the other through respective pressure-generating and pressure-releasing strokes; and
   (c) at least one resiliently yieldably deformable annular member mounted on said drawbar and disposable within the vessel portion to be tested when the vessel is received over said sleeve outer end, said deformable member having opposite ends and being mounted between and in contact at its opposite ends with said outer end of said sleeve and said outer end of said drawbar;
   (d) said deformable member being adapted to expand radially so as to apply expansive mechanical pressure against the interior of the vessel portion to be tested upon relative movement of said sleeve and drawbar through said pressure-generating stroke which causes relative movement of said sleeve outer end and said drawbar outer end toward one another and thereby application of compressive force against said opposite ends of said deformable member;
   (e) said deformable member being adapted to contract radially so as to release application of the mechanical pressure against the interior of the vessel portion to be tested upon relative movement of said sleeve and drawbar through said pressure-releasing stroke which causes relative movement of said sleeve outer end and said drawbar outer end away from one another and thereby release of application of compressive force against said opposite ends of said deformable member.

2. The apparatus of claim 1 further comprising:
   (e) means attached to said deformable member for sensing the mechanical pressure applied by said deformable member against the interior of the vessel portion to be tested.

3. The apparatus of claim 1 wherein said deformable annular member is one or more ring-shaped elements composed of elastomer material.

4. The apparatus of claim 1 wherein said outer end of said sleeve is in the form of a first annular end plate.

5. The apparatus of claim 4 wherein said outer end of said drawbar is in the form of a second annular end plate axially spaced from said first annular end plate on said sleeve.

6. The apparatus of claim 5 wherein deformable annular member mounted on said drawbar is mounted between said first en plate on said sleeve and said second end plate on said drawbar, said deformable member having its axially displaced opposite ends disposed respectively in contact with said first and second end plates.

7. The apparatus of claim 6 wherein said deformable annular member is one or more ring-shaped elements composed of elastomer material.

8. An apparatus for pressure burst testing of a hollow vessel, comprising:
   (a) a frame;
   (b) reciprocable means mounted on said frame and being operable for reciprocal movement through pressure-generating and pressure-releasing strokes;
   (c) power means connected to said reciprocable means and being actuatable to drive said reciprocable means through its respective strokes; and
   (d) a test mandrel mounted on said frame and being aligned with said reciprocable means, said test mandrel including
      (i) a hollow sleeve having an outer end adapted to receive thereover a hollow vessel such that a portion of the vessel to be tested extends beyond said sleeve outer end,
      (ii) an elongated member disposed within said hollow sleeve and attached to said reciprocable mean, said member having an outer end extending beyond said outer end of said hollow sleeve and being coextensible with the vessel portion to be tested when the vessel is received over said sleeve outer end, said elongated member being movable relative to said sleeve with movement of said reciprocable means through its respective strokes, and
      (iii) at least one resiliently yieldably deformable annular member mounted on said elongated member and disposable within the vessel portion to be tested when the vessel is received over said sleeve outer end, said deformable member having opposite ends and being mounted between and in contact at its opposite ends with said outer end of said sleeve and said outer end of said elongated member,
      (iv) said deformable member being adapted to expand radially so as to apply expansive mechanical pressure against the interior of the vessel portion to be tested upon movement of said reciprocable means and said elongated member therewith through said pressure-generating stroke relative to said sleeve which causes movement of said sleeve outer end toward said elongated member outer end and thereby application of compressive force against said opposite ends of said deformable member,
      (v) said deformable member being adapted to contract radially so as to release application of the mechanical pressure against the interior of the vessel portion to be tested upon movement of said reciprocable means and said elongated member therewith through said pressure-releasing stroke relative to said sleeve which causes movement of said sleeve outer end away from said elongated member outer end and thereby release of application of compressive force against said opposite ends of said deformable member.

9. The apparatus of claim 8 further comprising:
   (e) means attached to said deformable member for sensing the mechanical pressure applied by said deformable member against the interior of the vessel portion to be tested.

10. The apparatus of claim 8 wherein said power means includes means operable for causing movement of said reciprocable means and said elongated member therewith through said pressure-generating stroke relative to said sleeve at a predetermined rate which causes application of a gradually increasing magnitude of pressure by said deformable member against the interior of the vessel portion to be tested so as to provide a static mode of pressure burst testing thereof.

11. The apparatus of claim 8 wherein said power means includes means operable for causing movement of said reciprocable means and said elongated member therewith through said pressure-generating stroke relative to said sleeve at a predetermined rate which causes application of an instantaneously increasing magnitude of pressure by said deformable member against the interior of the vessel portion to be tested so as to provide a dynamic mode of pressure burst testing thereof.

12. The apparatus of claim 8 wherein said reciprocable means is a hydraulic cylinder assembly.

13. The apparatus of claim 12 wherein said hydraulic cylinder assembly includes:
   a hollow cylinder housing mounted on said frame and having opposite forward and rearward ends; and
   a piston mounted in said cylinder housing in spaced relation to and between said opposite ends thereof and being reciprocally movable within said cylinder housing through said pressure-generating and pressure-releasing strokes.

14. The apparatus of claim 13 wherein said power means is connected in communication with said opposite ends of said cylinder housing and is actuatable to drive said piston through said respective strokes.

15. The apparatus of claim 13 wherein said hollow sleeve of said test mandrel is stationarily mounted on said frame and connected at an inner end to said cylinder housing.

16. The apparatus of claim 13 wherein said elongated member of said test mandrel is a drawbar disposed coaxially within said sleeve, said drawbar being rigidly attached at an inner end to said piston.

17. The apparatus of claim 8 wherein said outer end of said sleeve is in the form of a first annular end plate.

18. The apparatus of claim 17 wherein said outer end of said elongated member is in the form of a second annular end plate axially spaced from said first annular end plate on said sleeve.

19. The apparatus of claim 18 wherein deformable annular member mounted on said elongated member is mounted between said first end plate on said sleeve and said second end plate on said elongated member, said deformable member having its axially displaced opposite ends disposed respectively in contact with said first and second end plates.

20. The apparatus of claim 8 wherein said deformable annular member is one or more ring-shaped elements composed of elastomer material.

21. An apparatus for pressure burst testing of a hollow vessel, comprising:

(a) a frame;

(b) a hydraulic cylinder assembly including (i) a hollow cylinder housing mounted on said frame and having opposite forward and rearward ends, and (ii) a piston mounted in said cylinder housing in spaced relation to and between said opposite ends thereof and being operable for reciprocal movement within said cylinder housing through pressure-generating and pressure-releasing strokes;

(c) power means connected in communication with said opposite ends of said cylinder housing and being actuatable to drive said piston through its respective strokes; and (d) a test mandrel coaxially aligned with said hydraulic cylinder assembly, said test mandrel including (i) an elongated hollow sleeve stationarily mounted on said frame and having an inner end connected to said cylinder housing and an outer end adapted to receive thereover a hollow vessel such that a portion of the vessel to be tested extends beyond said sleeve outer end, (ii) a first end plate attached on said outer end of said sleeve, (iii) an elongated drawbar disposed coaxially within said sleeve, said drawbar having an inner end being rigidly attached to said piston and at an opposite outer end extending beyond said outer end of said hollow sleeve coextensible with the vessel portion to be tested, said drawbar being movable relative to said hollow sleeve upon movement of said piston through its respective strokes, (iv) a second end plate attached on said outer end of said drawbar and spaced axially from said first end plate on said outer end of said sleeve, and (v) at least one resiliently yieldably deformable annular member mounted on said drawbar and disposable within the vessel portion to be tested, said deformable member being mounted between said first end plate on said outer end of said sleeve and said second end plate on said outer end of said drawbar, said deformable member having axially displaced opposite ends disposed respectively in contact with said first and second end plates, (vi) said deformable member being adapted to expand radially so as to apply expansive mechanical pressure against the interior of the vessel portion to be tested upon movement of said piston and said drawbar therewith through said pressure-generating stroke relative to said sleeve which causes movement of said second end plate toward said first end plate and thereby application of compressive force against said opposite ends of said deformable member, (vii) said deformable member being adapted to contract radially so as to release application of the mechanical pressure against the interior of the vessel portion to be tested upon movement of said piston and said drawbar therewith through said pressure-releasing stroke relative to said sleeve which causes movement of said second end plate away from said first end plate and thereby release of application of compressive force against said opposite ends of said deformable member.

22. The apparatus of claim 21 further comprising:

(e) means attached to said deformable member for sensing the mechanical pressure applied by said deformable member against the interior of the portion of the hollow vessel to be tested.

23. The apparatus of claim 21 wherein said power means includes means operable for causing movement of said piston and said drawbar therewith through said pressure-generating stroke relative to said sleeve at a predetermined rate which causes application of a gradually increasing magnitude of pressure by said deformable member against the interior of the vessel portion to be tested so as to provide a static mode of pressure burst testing thereof.

24. The apparatus of claim 21 wherein said power means includes means operable for causing movement of said piston and said drawbar therewith through said pressure-generating stroke relative to said sleeve at a predetermined rate which causes application of an instantaneously increasing magnitude of pressure by said deformable member against the interior of the vessel portion to be tested so as to provide a dynamic mode of pressure burst testing thereof.

25. The apparatus of claim 21, wherein said deformable member is a plurality of ring-shaped elements composed of elastomer material.

26. A method for pressure burst testing of a hollow vessel, comprising the steps of:

(a) providing a drawbar and a hollow open-ended sleeve in reciprocally movable relation to one another and with the drawbar extending through the sleeve such that an outer end of the drawbar extends beyond an outer end of the sleeve;

(b) providing a resiliently yieldably deformable annular member about the drawbar between and in contact with an outer end of the sleeve and an outer end of the drawbar;

(c) disposing a hollow vessel over the outer end of the sleeve such that a portion of the vessel to be tested extends beyond the sleeve outer end and over the deformable member mounted on the drawbar outer end;

(d) moving the drawbar and sleeve relative to one another through a pressure-applying stroke so as to move the drawbar outer end and the sleeve outer end toward one another and apply a compressive force against opposite ends of the deformable member, causing the member to expand radially and apply an expansive mechanical pressure against the interior of the vessel portion to be tested; and (e) moving the drawbar and sleeve relative to one another through a pressure-releasing stroke so as to move the drawbar outer end and the sleeve outer end away from one another and release application of the compressive force against opposite ends of the deformable member, allowing the member to contract radially and release application of the mechanical pressure against the interior of the vessel portion.

27. The method of claim 26 further comprising the step of:

(f) sensing the mechanical pressure applied by the deformable member against the interior of the vessel portion to be tested.

28. A method for pressure burst testing of a hollow vessel, comprising the steps of:

(a) providing a drawbar mounted for reciprocal movement relative to a hollow open-ended stationary sleeve and through the sleeve such that an outer end of the drawbar extends beyond an outer end of the sleeve;

(b) providing a resiliently yieldably deformable annular member mounted on the drawbar between and in contact with an end plate on the outer end of the sleeve and an end plate on the outer end of the drawbar;

(c) disposing a hollow vessel over the outer end of the stationary sleeve such that a portion of the vessel to be tested extends beyond the sleeve outer end and over the deformable member mounted on the drawbar outer end;

(d) moving the drawbar relative to the sleeve through a pressure-applying stroke so as to move the drawbar end plate toward the sleeve end plate and apply a compressive force against opposite ends of the deformable member, causing the member to expand radially and apply an expansive mechanical pressure against the interior of the vessel portion to be tested; and (e) moving the drawbar relative to the hollow sleeve through a pressure-releasing stroke so as to move the drawbar end plate away from the sleeve end plate and release application of the compressive force against opposite ends of the deformable member, allowing the member to contract radially and release application of the mechanical pressure against the interior of the vessel portion.

29. The method of claim 28 further comprising the step of:
(f) sensing the mechanical pressure applied by the deformable member against the interior of the vessel portion to be tested.

30. The method of claim 28 wherein the drawbar is moved relative to the sleeve at a predetermined rate which causes application of a gradually increasing magnitude of pressure by the deformable member against the interior of the vessel portion so as to provide a static mode of pressure burst testing thereof.

31. The method of claim 28 wherein the drawbar is moved relative to the sleeve at a predetermined rate which causes application of an instantaneously increasing magnitude of pressure by the deformable to provide a dynamic mode of pressure burst testing thereof.

* * * * *

UNITED STATES PATENT AND TRADEMARK OFFICE
CERTIFICATE OF CORRECTION

PATENT NO. : 4,793,179
DATED : December 27, 1988
INVENTOR(S) : Ernest M. Carlson It is certified that error appears in the above-identified patent and that said Letters Patent is hereby corrected as shown below:

In claim 6, line 9, delete "en" and substitute --end--.

In claim 8, line 35, delete "mean" and substitute --means--.

In claim 31, line 23, after "deformable" insert --member against the interior of the vessel portion so as--.

Signed and Sealed this

Fourth Day of April, 1989

Attest:

Attesting Officer

DONALD J. QUIGG

Commissioner of Patents and Trademarks